United States Patent [19]
DelGiorno et al.

[11] Patent Number: 4,819,485
[45] Date of Patent: Apr. 11, 1989

[54] MUSCLE TESTING APPARATUS

[75] Inventors: Daniel DelGiorno, Fort Salonga; Russell A. Pellicano, North Bay Shore; Henry Medina, Melville, all of N.Y.

[73] Assignee: Myo-Tech Corp., Boca Raton, Fla.

[21] Appl. No.: 869,135

[22] Filed: May 30, 1986

[51] Int. Cl.⁴ ............................................. A61B 5/22
[52] U.S. Cl. ................................................... 73/379
[58] Field of Search .......................... 73/379, 380, 381

[56] References Cited

U.S. PATENT DOCUMENTS

| | | |
|---|---|---|
| 2,255,711 | 9/1941 | Noor . |
| 2,342,019 | 2/1944 | Solinski . |
| 2,590,055 | 3/1952 | Timmerman . |
| 2,644,334 | 7/1953 | Perry . |
| 2,680,967 | 6/1954 | Newman . |
| 2,860,514 | 11/1958 | Lauru . |
| 3,045,667 | 7/1962 | Sellner et al. . |
| 3,081,634 | 3/1963 | Blaszkowski . |
| 3,158,028 | 11/1964 | Chope ................................. 73/724 |
| 3,174,343 | 3/1965 | Kasulis . |
| 3,285,070 | 11/1966 | McDonough . |
| 3,297,021 | 1/1967 | Davis et al. . |
| 3,374,675 | 3/1968 | Keropian ..................... 73/862.58 X |
| 3,375,717 | 4/1968 | Impellizzeri et al. . |
| 3,395,698 | 8/1968 | Morehouse . |
| 3,442,132 | 5/1969 | De Mare . |
| 3,465,592 | 9/1969 | Perrine . |
| 3,474,776 | 10/1969 | O'Brien . |
| 3,670,573 | 6/1972 | Kroemer . |
| 3,717,857 | 2/1973 | Evans . |
| 3,752,144 | 8/1973 | Weigle, Jr. . |
| 3,894,437 | 7/1975 | Hagy et al. . |
| 3,995,492 | 12/1976 | Clynes . |
| 4,114,449 | 9/1978 | Dikeman et al. . |
| 4,231,255 | 11/1980 | Haski et al. . |
| 4,307,608 | 12/1981 | Useldinger et al. . |
| 4,333,340 | 6/1982 | Elmeskog . |
| 4,462,252 | 7/1984 | Smidt et al. . |
| 4,501,148 | 2/1985 | Nicholas et al. . |
| 4,534,557 | 8/1985 | Bigelow et al. . |
| 4,592,371 | 6/1986 | Pellicano et al. ................. 73/379 X |
| 4,614,479 | 9/1986 | Liu ......................................... 417/44 |

Primary Examiner—Charles A. Ruehl
Attorney, Agent, or Firm—Wolder, Gross & Yavner

[57] ABSTRACT

Apparatus for testing the strengths of muscle and muscle groups of a person. In use, an inflated pressure pad is engaged with a body area, and a force from a muscle or muscle group is applied to the pad. This force is sensed and a signal representing that force is displayed. The pressure pad is connected to the guide so that the pad may be fixed in a multitude of different positions to engage many different body areas subjected to forces from a multitude of different muscles and muscle groups.

16 Claims, 6 Drawing Sheets

OPERATING TABLES

NOR GATE

| INPUT CONNECTIONS | | OUTPUT CONNECTION |
|---|---|---|
| a | b | c |
| + | + | 0 |
| + | 0 | 0 |
| 0 | + | 0 |
| 0 | 0 | + |

AND GATE

| INPUT CONNECTIONS | | OUTPUT CONNECTION |
|---|---|---|
| a | b | c |
| + | + | + |
| + | 0 | 0 |
| 0 | + | 0 |
| 0 | 0 | 0 |

+ = HIGH VOLTAGE LEVEL
− = LOW VOLTAGE LEVEL

OPERATING TABLE FOR FLIP-FLOP 412 OF CIRCUIT 400

| INPUT CONNECTIONS | | OUTPUT CONNECTION | |
|---|---|---|---|
| a | b | c | |
| 0 | 0 | 0 | OUTPUT CONNECTION REMAINS AT A LOW VOLTAGE LEVEL UNTIL BOTH INPUT CONNECTIONS CHANGE TO A HIGH VOLTAGE LEVEL, AND THEN THE OUTPUT CONNECTION CHANGES TO A HIGH VOLTAGE LEVEL. |
| 1 | 1 | 1 | OUTPUT CONNECTION REMAINS AT A HIGH VOLTAGE LEVEL UNTIL BOTH INPUT CONNECTIONS CHANGE TO A LOW VOLTAGE LEVEL, AND THEN THE OUTPUT CONNECTION CHANGES TO A LOW VOLTAGE LEVEL. |

+ = HIGH VOLTAGE LEVEL
0 = LOW VOLTAGE LEVEL

FIG. 13

MUSCLE TESTING APPARATUS

BACKGROUND OF THE INVENTION

This invention generally relates to apparatus for testing and indicating the strengths of muscles; and, more specifically, to apparatus especially well-suited to test and indicate the strengths of individual muscles.

Recently, equipment has been developed to objectively and quantitatively measure the strength of individual muscles. As a therapeutic tool, such devices are very helpful in that they help a therapist identify specific muscles that need to be strengthened and to design a program that will help those particular muscles. Moreover, a quantitative measurement will tell not only which muscles are weak, but also how weak those muscles are. Further, as a person is undergoing treatment, an objective measure of the progress he or she is making, first, helps the therapist modify the treatment program, if necessary, and second, allows the patient to witness personally the fact that his or her muscles are getting stronger with therapy, which often encourages the patient to continue the treatment. In addition, often a patient may believe he or she is fully recovered and will discontinue treatment. An accurate, quantitative and objective measure of the strength of each muscle may show otherwise, however, and convince the patient to continue treatment.

As an exercise training tool, an objective and quantitative measurement of the strength of individual muscles will help a person or a trainer develop a highly personalized exercise program that concentrates on the muscles that need the most work. Occasional retesting will enable an individual to observe personally the progress he or she is making, and will help show how effective a particular exercise program is and, if it becomes advisable to do so, how a program should be modified. An individual may test and record the strengths of his or her muscles while healthy to provide a personal standard; and if that person is later injured, he or she, while recovering, can compare his or her muscle strengths against that recorded standard to determine whether the muscles have adequately recovered before resuming a particular activity, thus lessening the risk of a re-injury or of a new injury.

Prior art devices for testing and indicating the strengths of individual muscles are somewhat cumbersome to use. To elaborate, these devices are normally changed from one position to another to test different muscles, but usually kept in a fixed position while any one particular muscle is being tested. With prior art devices, it is sometimes difficult and time consuming to position the device properly to test some muscles; and, while testing certain muscles, it is likewise occasionally difficult to keep the device in the desired, fixed position. Indeed, because of these difficulties, prior art devices are, as a practical matter, not effective to test certain muscles.

Moreover, prior art devices provide an indication of the force being developed by a particular muscle at a given instant in time, and this gives information about the strength of the muscle. While this is useful information, having an objective and quantitative indication of the strength and endurance of a muscle over a period of time such as 30 or 40 seconds, would normally be much more helpful to a trainer or a therapist.

SUMMARY OF THE INVENTION

An object of the present invention is to provide a muscle testing apparatus that is very simple to move between a multitude of different positions to test the strengths of different muscles and muscle groups, and yet is easy to hold rigidly in each of those positions.

Another object of this invention is to provide a muscle testing apparatus with a pressure sensing pad that may be moved between and securely held in a multitude of different positions to engage many different muscles and muscle groups; and where, for each of these positions, a face of the pad may be located at least substantially perpendicular to the direction of the force developed by the muscle or muscle group being tested.

A further object of the present invention is to provide a muscle testing apparatus that produces an objective and quantitative indication of the amount of force developed by a muscle over a period of time.

These other objectives are attained with apparatus for testing the strength of muscles and muscle groups of a person, and comprising a guide means, an inflatable pressure pad, sensing and display means, and connecting means. The pressure pad is provided to engage body areas of a person subjected to forces from his or her muscles and muscle groups, and the sensing and display means is connected to the pressure pad to sense the force applied thereto and to display a signal representing that force. The connecting means connects the pressure pad to the guide means, and is adjustable between locked and unlocked positions. In the locked position, the connecting means securely holds the pressure pad in a fixed position relative to the guide means; and in the unlocked position, the connecting means supports the pressure pad for movement along the guide means, and pivotal movement about a horizontal axis. With this maneuverability, it is very easy to position the pressure pad at a multitude of locations to engage many different body areas subjected to forces from a multitude of different muscles and muscle groups.

Preferably, the sensing and display means includes a pressure transducer, a variable capacitance oscillator, a pulse counter, counter control means, and display means. The transducer generates an electric current proportional to the extent to which the pressure on the pad exceeds a threshold pressure, and the variable capacitance oscillator generates electric current pulses at a variable frequency dependent on the magnitude of the current generated by the transducer. The pulse counter counts the electric pulse signals generated by the oscillator, the counter control means controls the counter to count only those pulses from the oscillator that are generated during a test period, and the display means displays the number of pulse signals counted by the counter during a test period. Preferably, the muscle and testing apparatus further includes a pump to pressurize the pressure pad, and a pump control circuit may be provided to activate the pump and to deactivate the pump automatically when the pressure in the pad reaches a preset level.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIGS. 9a–9g illustrate several applications of the apparatus of this invention.

DETAILED DESCRIPTION OF THE PREFERRED EMBODIMENTS

Figure 1:
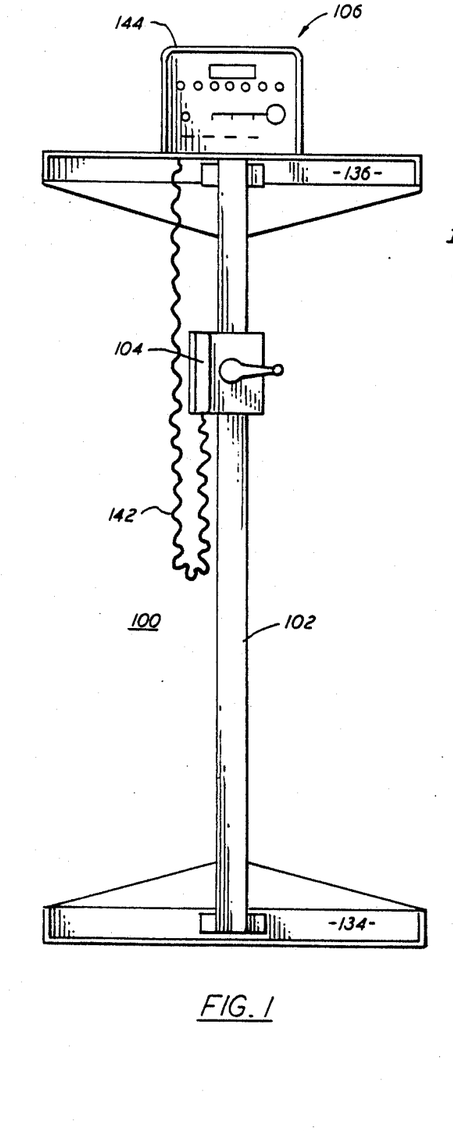
FIG. 1 is a front view of an apparatus constructed in accordance with the present invention.
Figure 2:
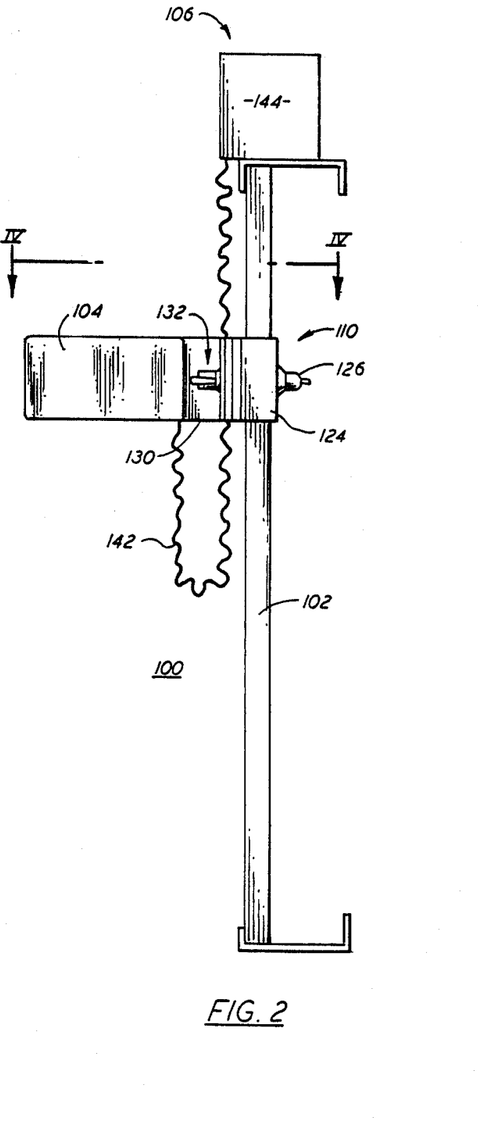
FIG. 2 is a side view of the apparatus shown in FIG. 1.

FIGS. 1 and 2 illustrate muscle testing apparatus 100 generally comprising guide means 102, pressure pad 104, sensng and display means 106, and connecting means 110. Preferably, with reference to FIG. 3, sensing and display means 106 includes pressure transducer 112, variable capacitance oscillator 114, counter 116, counter control means 120, and display means 122. With reference to FIGS. 1, 2 and 4–6, connecting means 110 includes slide assembly 124, means 126 connecting that assembly to guide means 102, support arm 130, and means 132 connecting that arm to the slide assembly.

Guide means 102 is provided to guide movement of pressure pad 104 along a predefined path, and for example the guide means may comprise a vertically extending post. In use, guide means 102 itself may be supported in any acceptable way. For instance, first bracket 134 may securely connect a lower end of guide means 102 to a floor or a wall, and second bracket 136 may securely connect an upper end of the guide means to that wall or to a ceiling. Guide means 102 and brackets 134 and 136 may be made from numerous materials, and may have a variety of shapes and sizes, although preferably the guide means has a non circular horizontal cross-section to help prevent slide assembly 124 from pivoting or swinging around the guide means. The embodiment of guide means 102 shown in FIGS. 1 and 2 is made from aluminum and has a hollow, rectangular horizontal cross-sectional shape.

Figure 7:
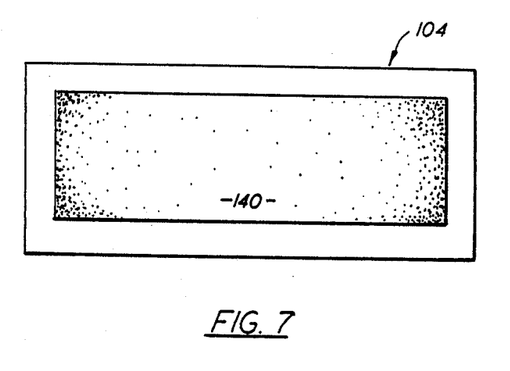
FIG. 7 is a rear view of the pressure pad used in the apparatus of FIGS. 1 and 2.

Pressure pad 104 is provided to engage body areas of a person subjected to forces from his or her muscles and muscle groups. With reference to FIGS. 1, 2 and 7, preferably, pad 104 comprises an inflatable flexible bag having a generally flat rectangular shape, forming front and back generally planar front and back faces. Pad 104 may be made from any suitable material such as rubber; and with a preferred embodiment, a flat strip 140 of hook and snap type fasteners, such as velcro, is connected to the back face of the pressure pad to hold the pad in place in apparatus 100, in a manner discussed in detail below. In use, pad 104 is filled with a gas, such as ambient air, to a preset pressure.

Sensing and display means 106 is connected to pressure pad 104 to sense the force applied to that pad and to generate a signal providing a quantitative measure of that force. With the preferred sensing and display means 106 illustrated in FIG. 3, pressure transducer 112 is connected to pressure pad 104 via line 142 (shown in FIGS. 1 and 2) so that the pressure on the transducer is equal to the pressure in the pressure pad, and the transducer generates an electric current proportional to the extent to which the pressure on the transducer exceeds a threshold pressure.

Figure 3:
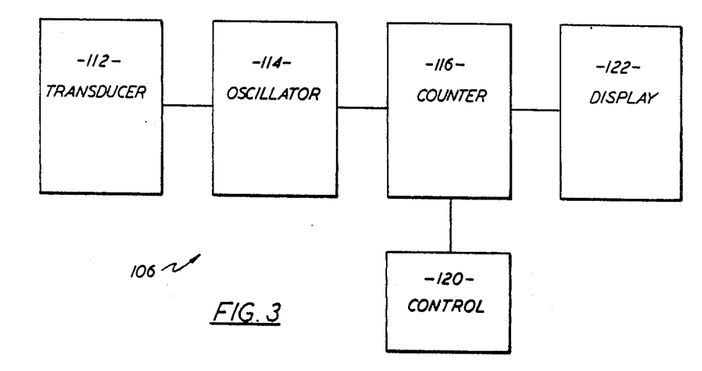
FIG. 3 is a block diagram showing the sensing and display means of the apparatus of FIGS. 1 and 2.

Variable capacitance oscillator 114 is connected to transducer 112 to receive the current generated thereby, and the oscillator generates an electric current pulse at a variable frequency dependent on the magnitude of the current conducted to the oscillator. In particular, the frequency of this current pulse increases and decreases, although not necessarily linearly, with the magnitude of the current generated by the transducer 112.

Counter 116 is connected to variable capacitance oscillator 114 to count the electric pulse signals generated by the oscillator. More specifically, counter 116 is an electronic device having a multitude of states; and each time the counter receives an electric current pulse from oscillator 114, the counter changes from one state to the next. Hence, up to the maximum capacity of the counter, the state of the counter indicates the number of pulses that have been conducted to the counter. The output of counter 116 is an electric current dependent on the state of the counter, and thus that electric current is also indicative of the number of pulses that have been conducted to the counter.

Counter control means 120, described in detail below, is connected to and controls counter 116 to count only those pulses from oscillator 114 that are generated during a test period. In this way, the number of pulses counted by counter 116 provides a quantitative and objective indication of the amount of force applied to pressure pad 104 over that test period.

Display means 122 is connected to counter 116 to display the number of the electric pulse signal generated by variable capacitance oscillator 114 during a test period. Display means 122 receives the output signal from counter 116 and converts that output signal into one or more electric signal that are used to show a number that is equal to the number of pulse signals generated by oscillator 114. This number may be shown in a variety of different ways; and, for example, display means 122 may comprise a four character display board, with each character comprised of seven LED segments, designed to show the numbers 0 to 9999.

Pressures transducers, variable capacitance oscillators, pulse counters, and display means of the above-described types are all well-known devices. Any suitable devices of these types may be used to practice the present invention, and it is unnecessary to explain the details of these components further herein. Moreover, the various elements of sensing and display means 106 may be located in or connected to a protective housing 144, which in turn may be mounted on top bracket 136.

With reference again to FIGS. 1 and 2, connecting means 110 connects pressure pad 104 to guide means 102, and this connecting means is adjustable between locked and unlocked positions. In the locked position, connecting means 110 securely holds pressure pad 104 in a fixed position relative to guide means 102; and when connecting means 110 is in the unlocked position, pressure pad 104 is slideable along the guide means 102, and pivotally movable about a horizontal axis. With this mobility and maneuverability, pressure pad 104 may be easily adjusted between and securely held in a multitude of different positions, in which the pressure pad may be readily engaged by many different body areas to test the strengths of a multitude of different muscles and muscle groups. Moreover, for each of these positions of pressure pad 104, the front face thereof may be located at least substantially perpendicular to the direction of the force developed by the muscle or muscle group being tested.

Figure 4:
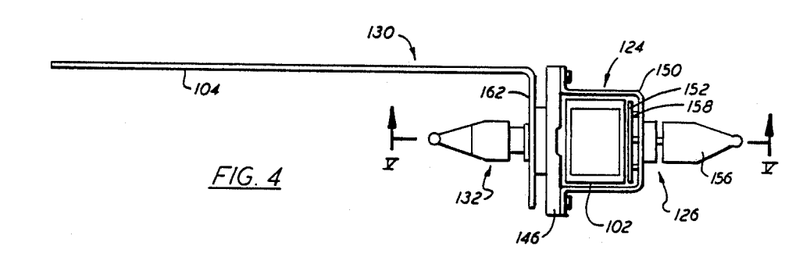
FIG. 4 is a top view of several connected parts of the apparatus shown in FIGS. 1 and 2, taken along line IV—IV of FIG. 2.
Figure 5:
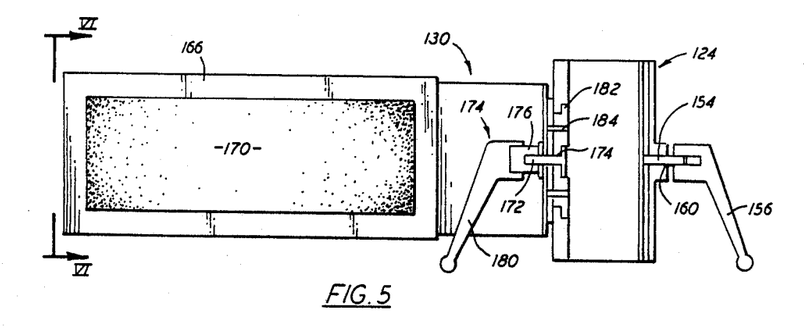
FIG. 5 is a side view, partially in cross-section taken along line V—V of FIG. 4.
Figure 6:
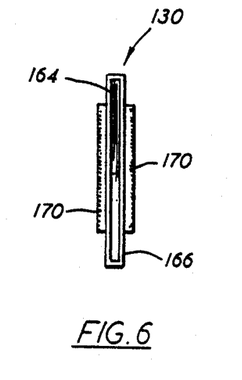
FIG. 6 is an end view of the support arm shown in FIGS. 4 and 5, taken along line VI—VI of FIG. 5.

As is believed best shown in FIGS. 4–6, slide assembly 124 of connecting means 110 is mounted on guide means 102, and preferably the slide assembly includes front plate 146 and U-shaped bracket 150 connected together to form a hollow enclosure extending around the outside of guide means 102. Connecting means 126 connects slide assembly 124 to guide means 102; and this connecting means 126 has a locked position securely holding slide assembly 124 in a fixed position on guide means 102, and an unlocked position wherein the slide assembly is slideable along the guide means. Preferably, this connecting means 126 comprises pressure plate 152, threaded pin 154, and handle 156. Plate 152 is located inside slide assembly 124, between the slide assembly and the back side of guide means 102, and the pressure plate is supported for movement toward and away from that guide means. For example, a plurality of guide pins 158 may be connected to pressure plate 152 and extend into bores in slide assembly 124 to support the pressure plate for movement toward and away from guide means 102.

Pin 154 is threaded through a threaded bore 160 in slide assembly 124, rearward of pressure plate 152. Pin 154 extends rearward of slide assembly 124, and handle 156 is securely mounted on this rearward end of the threaded pin. To lock slide assembly 124 to guide means 102, handle 156 and pin 154 are turned so that the pin advances in bore 160 and pushes plate 152 into a tight, secure pressure engagement with guide means 102, holding the entire assembly 124 rigidly in place. To unlock slide assembly 124, handle 156 and pin 154 are turned so that pin moves rearward in bore 160, releasing plate 152 from the pressure engagement with guide means 102, and allowing the slide assembly to slide along the guide means.

Support arm 130 extends away from slide assembly 124; and preferably, support arm 130 includes first and second legs 162 and 164, and sleeve 166. Legs 162 and 164 are connected together to form an L-shaped bracket, with the former leg located immediately forward of slide assembly 124, and with the latter leg extending outward from leg 162, substantially perpendicular thereto. Sleeve 166 extends around and is tightly fitted on leg 164, and thus forms front and rear faces; and flat, rectangular strips 170 of hook and snap type fasteners are secured to these faces of sleeve 166. Pressure pad 104 may be connected, by means of its own fastener strip 140, to either of strips 170, and thus may be located on either side of leg 164.

Connecting means 132 connects support arm 130 to slide assembly 124, and this connecting means 132 also has locked and unlocked positions. In its locked position, connecting means 132 securely holds support arm 130 in a fixed position relative to slide assembly 124; and in its unlocked position, connecting means 132 supports arm 130 for pivotal movement about a horizontal axis. This connecting means 132 preferably includes threaded screw 172 and clamping means 174. Slide assembly 124 forms a front central, through opening 174, leg 162 of support arm 130 forms an aligned opening, and screw 172 extends through these aligned openings. The head of screw 172 abuts against an inside surface of slide assembly 124 to hold the screw against forward movement, and clamping means 174 is threadably mounted on the forward end of screw 172, forward of leg 162.

To lock support arm 130 to slide assembly 124, clamping means 174 is rotated to move i rearward on screw 172 (toward guide means 102) to securely and tightly clamp leg 162 against the slide assembly. To unlock support arm 130 from slide assembly 124, clamping means 174 is rotated to move it forward on screw 172 (away from guide means 102) to release leg 162 from the pressure engagement against the slide assembly. In this unlocked position, screw 172 still supports arm 130, and the arm may be pivoted about the axis of the screw.

Clamping means 174 preferably comprises threaded socket 176 mounted on screw 172, and handle 180 mounted on that socket. Handle 180 may be mounted on socket by means of a pawl and a ratchet wheel so that the handle may be used to rotate the socket around screw 172 without requiring full rotation of the handle itself. A washer may be located between socket 176 and leg 162, and a clutch plate may be located between that leg and slide assembly 124.

Figure 8:
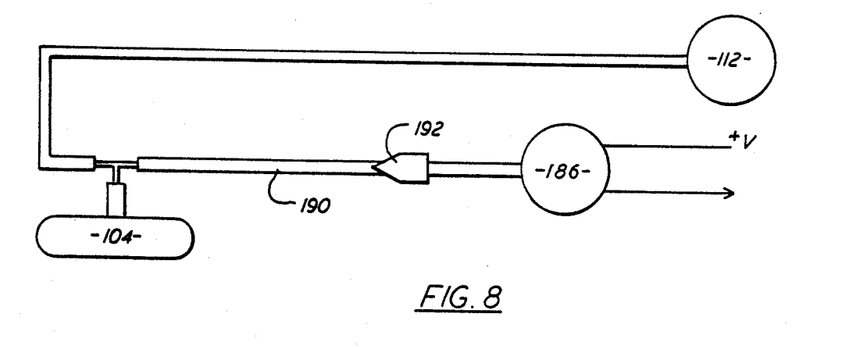
FIG. 8 is a schematic drawing showing a pump that may be used in the apparatus of this invention.
Figures 9A, 9B, 9C, 9D, 9E:
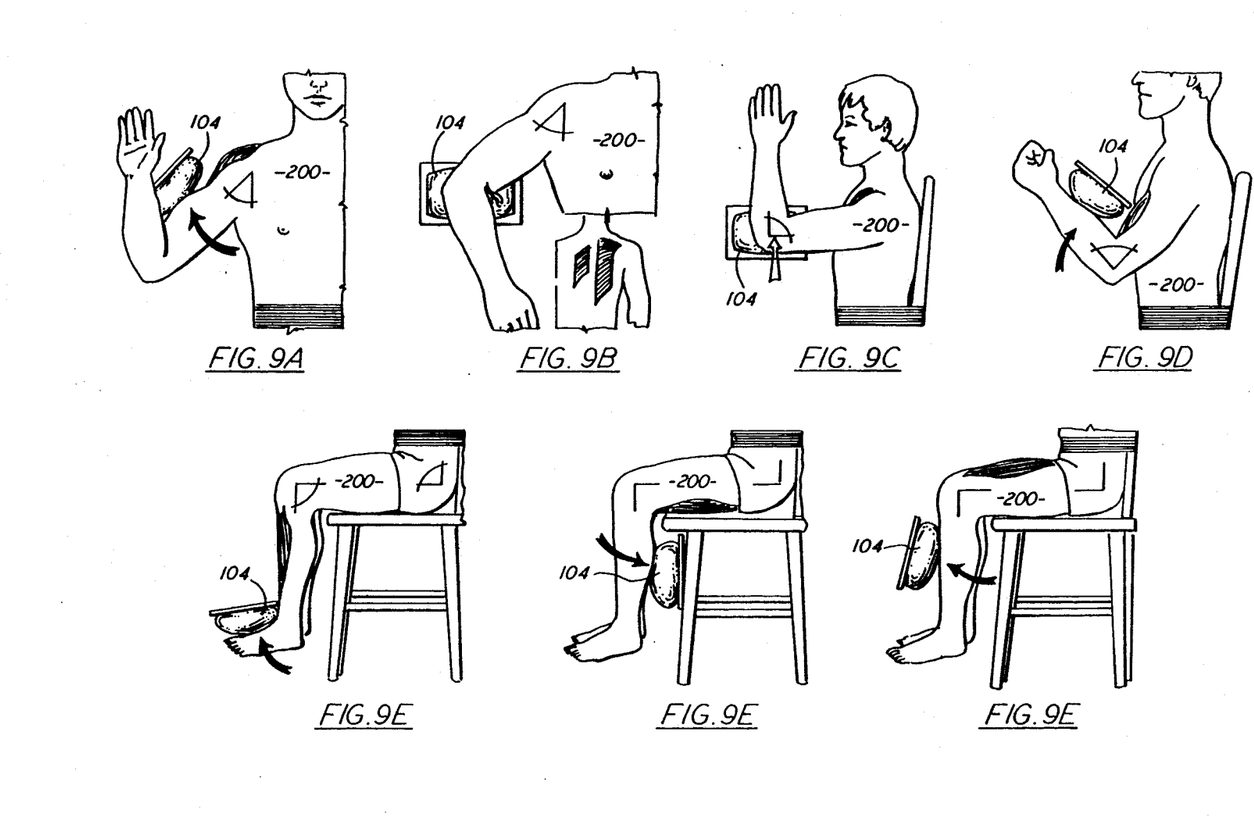

With a preferred embodiment of the invention, disk 182 and pins 184 may be used to help support arm 130 when connecting means 132 is in its unlocked position. To elaborate, plate 146 of slide assembly 124 forms a front circular opening, and disk 182 is located in this opening in a close, but movable, fit with the surfaces forming the opening so that the disk is rotatable within the opening about the axis of the disc. Disk 182 forms the central opening 174 of slide assembly 124, and this disk also forms a central recess at the end of that bore. The head of screw 172 seats in this recess, and the screw head causes the disk and the screw to rotate together about their common axis. Pins 184 are connected to leg 162 and extend therefrom into aligned sockets or openings in disk 182, and hence help support arm 130. Pins 184, of course, rotate with disk 182 and thus do not restrict pivotal movement of support arm 130. Preferably, plate 146 of slide assembly 124 includes a shoulder located directly forward of the outside portion of disk 182 to hold the disk against forward movement Preferably, apparatus 100 further includes a pump 186, schematically shown in FIG. 8, to pressurize pressure pad 104 More specifically, pump 186 is connected to the interior of pad 104 via line 190 to conduct pressurized air into the interior of the pad. This may be done occasionally, for example at the start of a day, to replace any air that might have escaped from the pressure pad 104 and to bring the pressure inside the pad to a preset or standard level. Any suitable pump may be used to do this, and the pump may also be located inside display housing 144. A one way check valve 192 may be located in line 190 to inhibit air from escaping from pad 104 through line 190. Preferably, pump 186 is electrically operated, and one electrical control circuit for the pump is described in detail below.

To prepare apparatus 100 for operation, guide means 102 is secured in place via brackets 134 and 136, and pump 186 may be used to bring the pressure in pad 104 to a desired level. To test a particular muscle or muscle group of a subject, the subject stands or sits next to apparatus 100, and pressure pad 104 is positioned so that it may be engaged by a body area that may be moved by that particular muscle or muscle group, with the front face of the pressure pad face perpendicular to the direction of the force developed by the muscle or muscle group. It is believed that best results are obtained if pad 104 is located at the middle of the arc, or range of motion, through which the body area would normally move as a result of the force applied to the body area by the muscle or muscle group being tested.

Pressure pad 104 is located in this particular position by locking slide assembly 124 at a selected height, and locking support arm 130 at a selected angle relative to the vertical. An operator may wish to record this selected height and angle; and guide means 102, slide assembly 124 and support arm 130 are provided with markings to indicate these measurements. Also, a graph or chart may be located on the floor adjacent apparatus 100 so that the operator can record the subject's position relative to the apparatus. In addition, it is desirable to position the subject and pad 104 to isolate the muscle or muscle group being tested; that is, to position the subject and the pressure pad so that only forces developed by the muscle or muscle group being tested are applied to the pressure pad. To accomplish this, when testing certain muscles or muscle groups, it may be preferred to have the patient sit in a chair with his or her legs raised off the ground or floor.

The subject then engages pad 104 with the body area. At the start of a test period, the subject flexes the muscle or muscle group under study to apply a force to pressure pad 104, and the subject continues to apply this force to the pressure pad until the end of the test period. The magnitude of the force applied to pressure pad 104 is sensed by sensing and display means 106, which produces a quantitative signal representing that force, and in particular, a quantitative signal representing the amount of the force applied to pressure pad 104 over the test period, which indicates the endurance of the muscle being tested. The results of the test may then be recorded and compared with the results of other tests to provide a quantitative comparison of changes in a patient's muscle or muscle group. For example, the test results may show that a particular muscle has become stronger as a result of an exercise program.

FIGS. 9a-9g illustrate seven application of muscle testing apparatus 100; and in particular, these figures show subject 200 and seven different positions of pressure pad 104 to test seven different muscle or muscle groups of the subject. FIG. 7a shows the positions of pad 104 and subject 200 to test the deltoid muscle; FIG. 7b, the trapezius and rhomboideus muscles; FIG. 7c, the pectoral major muscle; and FIG. 7d, the bicep muscle. FIG. 7e shows the position of pad 104 and subject 200 to test the ankle dorsi flexors muscle; FIG. 7f, the hamstring muscle; and FIG. 7g, the quadriceps muscle.

In one clinical program, apparatus 100 was used to test the above-identified seven muscle groups on twenty-three adult men and women. The ages of the subjects were between 21 and 60 years, with their mean age being 29.6 years. The subjects were all right handed, had not been under the care of a physician for at least the previous six months, and reported no medical complaints. During each testing session, four tests were conducted for each of the seven positions. The test period for two of these four tests was set at five seconds, the test period for the other two tests was set at ten seconds, and a one minute rest period was given between each test. Each subject underwent two testing sessions, with the first one followed seven to nine days later by the second session.

Pearson product moment correlations were used to evaluate reliability of the test scores for each of the seven positions. Reliability was assessed within a session (test 1 versus test 2 at the same test period) and between sessions (e.g. test 1 of session 1 versus test 1 of session 2). Within session reliability coefficients were very high, and the median value was 0.97 with only one coefficient out of 28 below a value of 0.90. Between-session reliability was also very good with most coefficients ranging between 0.79 and 0.92 (median=0.87). The one position at which the between-session reliability was lower was for ankle flexors, which had a median value of 0.65.

These data show that the apparatus of this invention provides highly reliable measures of six of the seven tested muscles and muscle groups, and it is believed that even this may be improved as the testing procedures are refined. These studies clearly show that the present invention may be effectively employed as a valuable tool in health and rehabilitation settings.

Apparatus 100 is relatively simple to build and operate, and it is very easy for both the operator and the patient to understand and conduct the above-described testing procedures. The test results are immediately available, and are easy to read, understand and interpret. The test results are objective and consistent, minimizing human variables and other subjective factors that are inherent in manual muscle testing procedures. Because the test results are objective and consistent, they help an operator determine the accuracy of subjective complaints from a patient, and they help to diagnose basic problems. For instance, the test results show quantitatively how weak different muscles are, and help to distinguish between muscle weaknesses caused by nerve damage from muscle weaknesses caused by strain.

Figure 10:
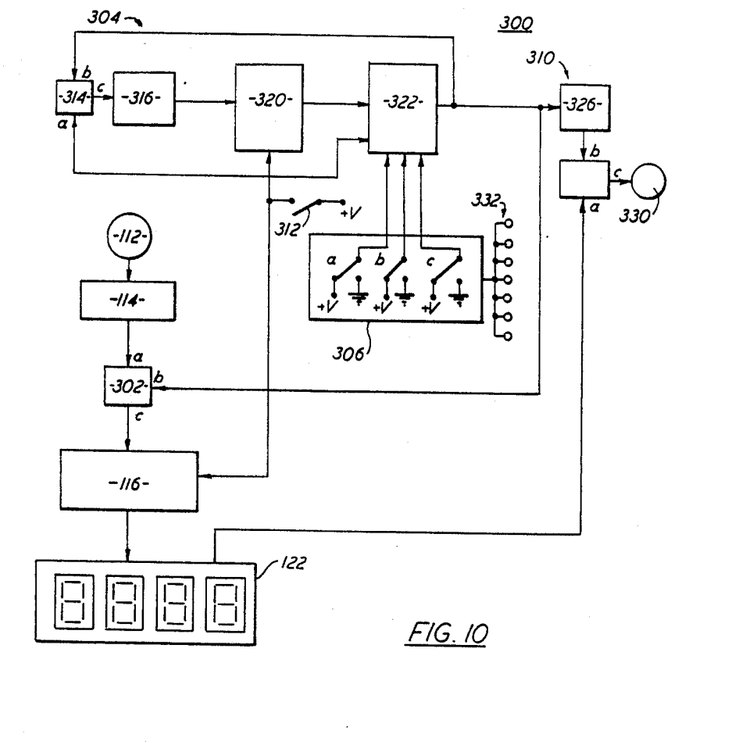
FIG. 10 is a schematic diagram of a control circuit for the counter illustrated in FIG. 3.

Control means 120 for counter 116 preferably comprises electric control circuit 300 shown in FIG. 10. Generally circuit 300 includes NOR gate 302 and timer means 304; and preferably the counter control circuit further includes means such as switch section 306 to select the length of the time period, and signal means 310 to indicate the end of a test period. With the embodiment of circuit 300 shown in FIG. 10, timer means 304 includes start switch 312, NOR gate 314, clock 316, up-counter 320, and test time comparator 322, and signal means 310 includes AND gate 324, pulse generator 326, and buzzer 330.

Figure 11:
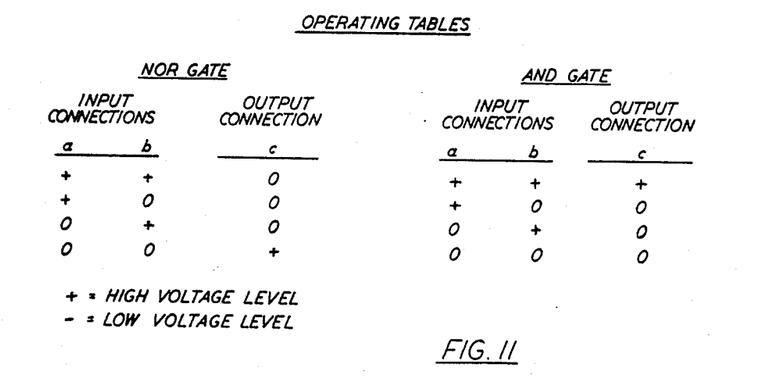
FIG. 11 is a chart summarizing the operations of several logic devices shown in FIG. 10.

NOR gates and AND gates are electronic logic devices having two input connections and one output connection, and their operations are summarized in FIG. 11. The output connection of of a NOR gate has a high voltage potential only when both input connections are at a low voltage potential; and, otherwise, the output of the NOR gate is at a low voltage potential. The output connection of an AND gate has a high voltage level only when both input connections of the gate are at a high voltage level, and otherwise the output of an AND gate is at a low voltage level.

First and second input connections 302a and 302b of the NOR gate 302 are connected to the output of oscillator 114 and to the output of timer means 304 respectively, and output connection 302c of the NOR gate is connected to counter 116. During a test period, timer means 304 conducts a low voltage potential to input connection 302b of NOR gate 302; and at the end of the test period, the timer means 304 conducts a high voltage signal to input connection 302b. In this way, with reference to FIG. 11, during a test period, when no electric pulse is being conducted to NOR gate input connection 302a from oscillator 114, the output connection 302c of the NOR gate is at a high voltage potential, and that potential drops to a low voltage potential when an electric pulse is conducted to input connection 302a. Output connection 302c remains at that low voltage potential as long as the pulse is conducted to input connection 302a; and, once that pulse ends, output connection 302c of NOR gate 302 returns to a high voltage potential. Each time output connection 302c changes from a low voltage potential to a high voltage potential, a new current is conducted to and counted by counter 116. Thus, the count kept by counter 116 increases by one at the end of each pulse generated by oscillator 114.

With the embodiment of timer means 304 shown in FIG. 10, between test periods, the output connection of test time comparator 322 is maintained at a high voltage level; and this output connection is connected to input connection 314b of NOR gate 314, maintaining that input connection at a high voltage level between test periods. As a result of this, NOR gate output connection 314c is kept at a low voltage level between test periods. To start a test period, start switch 312 is temporarily closed to generate a high voltage signal, and then re-opened to return the start switch output to a low voltage level. This temporary high voltage signal is conducted both to input connection 314a of NOR gate and to comparator 322, and this signal to the comparator resets that device so that the output thereof returns to a low voltage level. When this happens, input connection 314b of NOR gate 314 also falls to a low voltage level; and thus when start switch 312 is re-opened, both input connections 314a and 314b of NOR gate 314 are at a low voltage level.

This causes NOR gate output connection 314c to change to a high voltage level, and this activates clock 316. Clock 316 then generates current pulses at a regular frequency, and these pulses are conducted to up-counter 320. Counter 320 generates a continuous output current the magnitude of which depends on the number of pulses received from clock 316 since the last time the up-counter was reset. Hence, the magnitude of the current generated by up-counter 320 increases over a test period.

Test time comparator 322 is a conventional multi-plex chip, a first input of the comparator is connected to up-counter 320, and an output of the comparator is connected to input connection 302b of NOR gate 302. Comparator 322 receives the output current from up-counter 320 and compares the magnitude of that current to a preset current level. As long as the magnitude of the current from up-counter 320 is below the preset level, the output connection of comparator 322 is at a low voltage level. However, when the current from up-counter 320 exceeds the preset level, the output of comparator 322 switches to a high voltage level. This voltage level is conducted to NOR gate input connection 302b so that the voltage level of NOR gate output connection 302c changes to or remains at a low voltage level, and no further current pulses are conducted to counter 116. At this time, the number shown on display means 122 is then equal to the number of pulses generated by oscillator during the test period. The high voltage signal from comparator 326 is also conducted to NOR gate input connection 314b, causing output connection 314c of NOR gate 314 to change to a low voltage level, deactivating clock 316.

The output of comparator 322 remains at a high voltage level until it is reset, and this voltage signal both prevents NOR gate 302 from passing any further pulses to counter 116 and maintains clock 316 deactivated until the start of the next test period. Preferably, start switch 312 is also connected to reset input connections on counter 116 and up-counter 320 so that when the start switch is closed, the counter and up-counter are all reset to zero or initial states.

Switch section 306, including a plurality of switches 306a, 302b and 306c, may be provided to select the length of the test period. Each switch 306a, b and c is connected to comparator 322; and each switch has a high, or open, position (shown in FIG. 10) in which the switch conducts a high voltage signal to the comparator, and a low, or closed, position in which the switch conducts a low voltage signal to the comparator.

Each switch 306a, b and c may represent a different length of time and, for example, switches 306a, b and c may represent ten, twenty and forty seconds, respectively. When switch 306a is in its low state, and switches 302a, b and c are both in their high states, the test period is 10 seconds; when switch 306b is in its low state, and switches 306a and c are both in their high states, the test period is twenty seconds; and when switch 306c is in its low state, and switches 306a and b are both in their high states, the test period is forty seconds. Moreover, switches 306a, b and c may be used in an accumulative manner so that when switches 306a and b are in their low states, and switch 306c is in its high state, the test period is thirty seconds; and when switches 306b and c are in their low states and switch 306a is in its high state, the test period is sixty seconds.

Also, comparator 322 may be programmed so that the test period may be set to a seventh time length, such as five seconds, when all three switches 306a, b and c are in their high states. Comparator might further be programmed so that the test period is set to an eight time length when all three switches 306a, b and c are in their low states; however, preferably, this position of switches 306a, b and c is used to help actuate pump 186, as discussed in detail below. Control circuit 300 may be provided with a series of display lights 332, connected to switch section 306, to indicate the test time period that has been selected by the operator.

Clocks, up-counter, and multi-plex chips of the above-described types are all well known devices. Any suitable devices of these types may be used to practice the present invention, and it is unnecessary to explain the details of these components herein. Similarly, any suitable switches may be used as switches 306a, b and c and 312. Switches 306a, b and c may be single throw, double pole switches that will stay in either their state or their low states until manually changed. Preferably, switch 312 is a momentary switch, spring biased to an to an open position so that the switch must be forced to its closed position, and once released from that position, will automatically return to its open position.

During its operation, display means 122 produces a high frequency current signal, and this current is principally employed to operate the display shown by the display means. With circuit 300, this high frequency current is also used in signal means 310 to indicate the end of a test period. More specifically, a first input connection 324a of AND gate 324 is connected to display means 122 to receive that high frequency current signal therefrom. A second input connection 324b of the AND gate is connected to pulse generator 326, and output connection 324c, of the AND gate 324 is connected to buzzer 330.

Pulse generator 326 is connected to the output connection of test time comparator 322; and when that output connection changes from a low voltage level to a high voltage level, generator 326 generates one high voltage signal that lasts for about one second. Thus, during the duration of this one signal, the output connection 324c of AND gate 324 will alternate between high and low voltage levels in synchronization with the signal from display means 122. This alternating voltage level of output connection 324c causes an alternating current to pass through buzzer 330, generating an audible signal.

Figure 12:
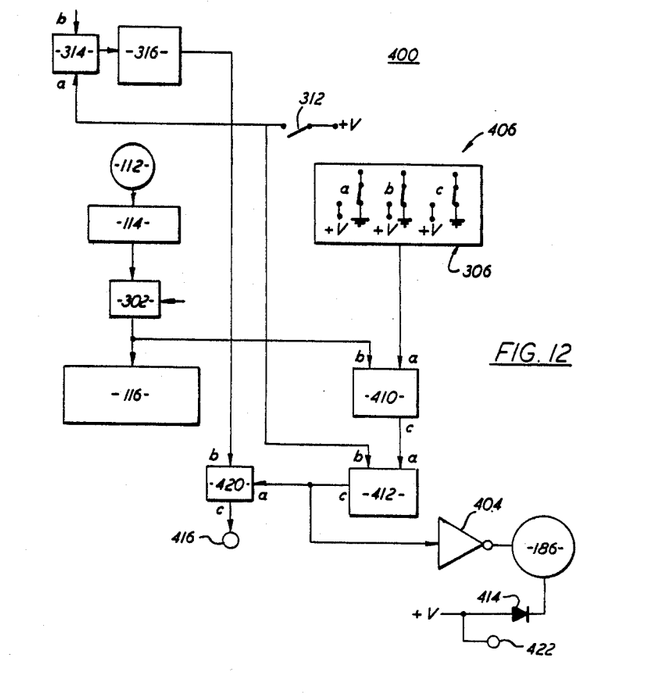
FIG. 12 is a schematic drawing of a control circuit for the pump illustrated in FIG. 8.

FIG. 12 schematically shows electric control circuit 400 for pump 186. Generally, pump 186 is electrically located in line 402, between a DC voltage source and ground (not shown), and pump control circuit 400 includes pump switch means 404 and switch control means 406. Switch control means 406 includes switch section 306, start switch 312, and NOR gate 302 discussed above in connection with counter control circuit 300; and the switch control means 406 further includes AND gate 410 and flip-flop 412. A diode 414 may be located in line 402 to keep the current passing through pump 186 below a preferred level.

Switch 404 has a pair of main terminals and a gate or trigger terminal. In the absence of any applied voltages, switch 404 assumes an open condition in which a very high impedance exists between its main terminals to effectively constitute an open switch. However, when a voltage of appropriate magnitude is applied to the gate terminal, switch 404 changes to a closed state in which a very low impedance is presented between its main terminals so that it essentially functions as a closed switch. Once rendered conductive, switch 404 will remain in a closed or conductive state, until the gate current drops below a certain level, at which time the switch returns to its open or off state. Thereafter, conduction through switch 404 will not occur until a triggering current of sufficient magnitude is again applied to the gate. Any suitable electronic switch, may be employed in the practice of this invention.

Switch control means 406 is electrically connected to the gate of switch means 404 to change that switch means between its open and closed states. A first input connection 410a of AND gate 410 is connected to switch section 306, a second input connection 410b of this AND gate is connected to the output connection 302c of NOR gate 302, and output connection 410c of the AND gate is connected to flip flop 412. Flip flops such as flip flop 412 of circuit 400, are electronic devices having a plurality of input connections and output connections and a number of characteristics. First, flip flops have a pair of output connections or signals that maintain an opposite relationship—when one of these output connections has a high voltage potential, the other output connection has a low voltage potential, and vise versa. Second, flip flops can be constructed so that, if certain input and output conditions exist, a change in the voltage level of only one of the input connections will have no affect on the voltage levels of the output connections of the flip-flop, and the voltage levels of output connections of such a flip-flop will remain fixed until the voltage levels of both input connections change.

Figure 13:
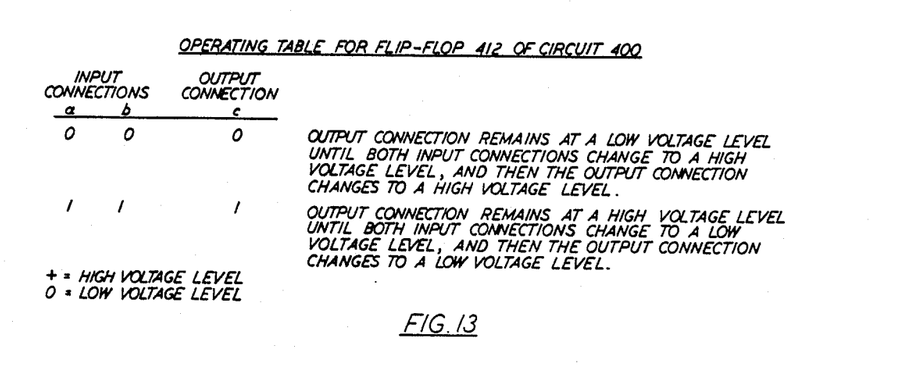
FIG. 13 is a chart showing the operation of the flip-flop of FIG. 12.

Only one of the output connections of flip-flop 412 is used in circuit 400, and this connection is connected to the gate of electronic switch 404. As previously mentioned, a first input connection 412a of flip-flop 412 is connected to output connection 410c of AND gate 410, and the second input connection 412b of the flip-flop is connected to start switch 312. FIG. 13 summarizes the operation of flip-flop 412. When inputs connections 412a and b are at low voltage levels, output connection 412c is at a low voltage level, and that output remains at this voltage level until both input connections 412a and b change to high voltage levels. When this happens, output connection 412c changes to a high voltage level, and this output remains at this voltage level until both inputs connections 412a and b change to a low voltage level, at which time the output connection also changes to a low voltage level.

To prepare circuit 400 to activate pump 186, switches 306a, b and c are all moved to their closed, or low, positions (shown in FIG. 12). Switch section 306 is designed so that, when these switches 306a, b and c are all closed, a high voltage level is developed at input connection 410a of AND gate 410. Then, start switch 312 is momentarily closed, and this causes a number of events to occur. First, 312 is closed, input connection 302b of NOR gate 302 is reset at a low voltage level. If, at this time, the pressure in pad 304 is below that at which transducer 112 generates a current, output connection 302c of NOR gate 302 and hence input connection 410b and gate 410 both change to high voltage levels. When this happens, output connection 410c of AND gate 410 and input connection 412a of flip-flop 412 change to high voltage states. Second, when switch 312 is closed, a high voltage level is developed at flip-flop input connection 412b; and this, in combination with the development of the high voltage level at flip-flop input connection 412a, causes a high voltage level to develop at flip-flop output connection 412c. This causes a current to be conducted to the gate of electronic switch 404, changing the switch to its closed state and actuating pump 186.

As soon as start switch 312 returns to its open position, input connection 412b of flip-flop 412 returns to a low voltage level. However, output connection 412c of flip-flop 412 remains at a high voltage level—and thus pump 186 remains activated—until both input connections 412a and b of the flip-flop fall to a low voltage level. As pump 186 operates, it increases the pressure in pad 104; and when a preset pressure is reached, transducer 112 generates a current. This current causes oscillator 114 to generate a pulse, bringing input connection 302a of NOR gate 302 to a high voltage level. This, in turn, causes output connection 302c of NOR gate 302 and input connection 410b of AND gate 410 to change to low voltage levels. When this happens, input connection 412a of flip-flop 412 falls to a low voltage level, and this causes output connection 412c of flip-flop 412 also to fall to a low voltage level, changing switch 404 to its open state and deactivating pump 186.

Pump control circuit 400 may be provided with a blinking light 416 to indicate that pump 186 is operating. To elaborate, a first input connection 420a of AND gate 420 is connected to output connection 412c of flip-flop 412, a second input connection 420b of the AND gate is connected to clock 316, and output connection 420c of AND gate 420 is connected to light 416. As previously mentioned, when start switch 312 is closed, a current is current is conducted to clock 316 to activate that device to generate current pulses, and these pulses are conducted to AND gate input connection 420b. At the same time, when flip-flop output connection 412c is at a high voltage level, which is the case when pump 186 is operating, input connection 420a of gate 420 is held constant at a high voltage level. Hence, under these conditions, output connection 420c of AND gate 420 changes between high and low voltage levels as input connection 420a changes between those levels, and consequently light 416 will blink in synchronization with the pulses from clock 316.

As will be understood by those of ordinary skill in the art, any suitable voltage sources may be used as the voltage sources shown in the drawings; and these voltage sources may all be connected to one primary source, such as a DC battery pack. An on-off switch (not shown) may be located in series between that voltage source and circuits 300 and 400, and a light 422 (shown in FIG. 12) may be provided to indicate whether that on-off switch is in its on or off position. In the case where the primary voltage source for pump 186 and circuits 300 and 400 is a DC battery pack, apparatus 100 may be provided with a battery charger that may be used to connect the battery pack to a conventional AC voltage source to charge the battery pack when apparatus 100 is not otherwise being used. Also, suitable energy sources (not shown) are provided for the electronic elements of circuits 300 and 400 including transducer 112, oscillator 14, counter 116, display 122, NOR gate 302, OR gate 314, clock 316, up-counter 320, comparator 322, AND gates 344, 410 and 416, and flip-flop 412.

While it is apparent that the invention disclosed herein is well calculated to fulfill the objects previously stated, it will be appreciated that numerous modifications and embodiments may be devised by those skilled in the art, and it is intended that the appended claims over all such modifications and embodiments as fall within the true spirit and scope of the present invention.

I claim:

1. Apparatus for testing the strength of muscles and muscle groups of a person, comprising:
    a guide means;
    an inflatable pressure pad to engage a body area of the person subjected to a force from a selected muscle or muscle group;
    sensing and display means connected to the pressure pad to sense the force applied to the pressure pad and to display a signal representing said force, said sensing and display means including means to provide a quantitative indication of the amount of force applied to the pressure pad over a test period, said indicating means including a pressure transducer connected to the pressure pad to generate a variable magnitude electric current in response to the force applied to the pressure pad;
    a variable capacitance oscillator connected to the pressure transducer to receive the electric current therefrom and to generate electric pulse signals at a frequency dependent on the magnitude of the electric current from the pressure transducer;
    a pulse counter connected to the variable capacitance oscillator to count the electric pulse signals generated thereby;
    a counter control circuit to control the counter to count only the pulse generated by the variable capacitance oscillator during the test period;
    display means connected to the counter to display the number of the electric pulse signals counted by the counter; and
    means connecting the pressure pad to the guide means, the connecting means being adjustable between a locked position securely holding the pressure pad in a fixed position relative to the guide means, and an unlocked position wherein the pressure pad is movable along the guide means, and pivotably movable about a horizontal axis to enable positioning of the pressure pad at a multitude of locations to engage a multitude of different body areas subjected to forces from a multitude of different muscles and muscle groups.

2. Apparatus according to claim 1, wherein the connecting means includes:
    a slide assembly mounted on the guide means;
    means connecting the slide assembly to the guide means, and having a locked position securely holding the slide assembly in a fixed position on the guide means, and an unlocked position wherein the slide assembly is slideable along the guide means;
    a support arm extending outward from the slide assembly; and
    means connecting the support arm to the slide assembly, and having a locked position securely holding the assembly, and an unlocked position wherein the support arm is pivotal about the horizontal axis.

3. Apparatus according to claim 2, wherein the means connecting the slide assembly to the guide means includes:
    a pressure plate supported by the slide assembly for movement toward and away from the guide means;
    a threaded pin threadably supported by the slide assembly for movement toward the guide means to move the pressure plate into a rigid, secure pressure engagement with the guide means, and for movement away from the guide means to release the pressure plate from said rigid pressure engagement; and
    a handle connected to the threaded pin to rotate the pin and move said pin toward and away from the guide means.

4. Apparatus according to claim 2, wherein:
the support arm includes an opening; and
the means connecting the support arm to the slide assembly includes
    (i) a threaded screw supported by the slide assembly, and extending therefrom through the opening of the support arm, and
    (ii) clamp means mounted on the screw, supported thereby for movement toward the slide assembly to clamp the support arm in a tight pressure engagement between the slide assembly and the clamp means, and supported by the screw for movement away from the slide assembly to release the support arm from said tight pressure engagement and to allow the support arm to pivot about said screw.

5. Apparatus according to claim 1, further comprising a pump connected to the pressure pad to conduct pressurized gas thereinto.

6. Apparatus according to claim 5, further comprising a pump control circuit to activate the pump and to deactivate the pump when the pressure in the pressure pad reaches a preset level.

7. Apparatus according to claim 1, wherein the counter control circuit includes:
- a NOR gate having first and second input connections, and an output connection;
- timer means to generate a low voltage signal during the test period and to generate a high voltage signal at the end of the test period;
- a first line connecting the variable capacitance oscillator to the first input of the NOR gate to conduct the electric pulses thereto;
- a second line connecting the timer means to the second input connection of the NOR gate;
- a third line connecting the output of the NOR gate to the counter means;
- whereby, during the test period, the NOR gate passes a high voltage signal to the counter each time the current pulse from the variable capacitance oscillator ends, and the output connection of the NOR gate is maintained at a low voltage level after the test period.

8. Apparatus according to claim 7, wherein, the timer means includes:
- a clock to generate pulses at a preset, regular frequency;
- an up-counter connected to the clock to receive the pulses therefrom, and generating a continuous current the magnitude of which is dependent on the number of pulses received from the clock during the test period;
- a comparator connected to the up-counter to receive the current generated thereby and to generate the high voltage signal of the timer means when the current from the up-counter reaches a preset magnitude.

9. Apparatus according to claim 8, wherein the timer means further includes a start switch to activate the clock.

10. Apparatus according to claim 9, wherein the counter control circuit further includes means to select the length of the test period.

11. Apparatus according to claim 1, further including means to select the length of the test period.

12. Control means for muscle testing apparatus of the type having a pressure pad to engage a body area of a person subjected to a force from a muscle or muscle group, the control means comprising:

- a pressure transducer connected to the pressure pad to generate a variable magnitude electric current in response to the force applied to the pressure pad;
- a variable capacitance oscillator connected to the pressure transducer to receive the electric current therefrom and to generate electric pulse signals at a frequency dependent on the magnitude of the electric current from the pressure transducer;
- a pulse counter connected to the variable capacitance oscillator to count the electric pulse signals generated thereby;
- a counter control circuit to control the counter to count only the pulses generated by the variable capacitance oscillator during the test period; and
- display means connected to the counter to display the number of the electric pulse signals counted by the counter.

13. Control means according to claim 12, further comprising:
- a NOR gate having first and second input connections, and an output connection;
- timer means to generate a low voltage signal during a test period and to generate a high voltage signal at the end of the signal;
- a first line connecting the variable capacitance oscillator to the first input connection of the NOR gate to conduct the electric pulse signals thereto;
- a second line connecting the timer means to the second input connection to the NOR gate;
- a third line connecting the output connection of the NOR gate to the counter means.

14. Control means according to claim 13, wherein the timer means includes:
- a clock to generate electric current pulses at a preset regular frequency;
- an up-counter connected to the clock to receive the pulses therefrom, and to generate a continuous current the magnitude of which is dependent on the number of pulses received from the generator during the test period; and
- a comparator connected to the up-counter to receive the current generated thereby and to generate the high voltage signal when the current from the up-counter reaches a preset magnitude.

15. Control means according to claim 12, further including a switch section to select the length of the test period.

16. Control means according to claim 15 for use with muscle testing apparatus having a pump connected to the pressure pad to conduct pressurized gas thereinto, the control means further comprising means to activate the pump and to deactivate the pump when the pressure in the pressure pad reaches a preset level.

* * * * *